United States Patent
Ramgopal et al.

(10) Patent No.: US 7,388,386 B2
(45) Date of Patent: Jun. 17, 2008

(54) METHOD AND APPARATUS FOR CORROSION DETECTION

(75) Inventors: Thodla Ramgopal, Karnataka (IN); J. Lawrence Nelson, Niskayuna, NY (US); Brian Lasiuk, Spring, TX (US); Mel Joseph Esmacher, Spring, TX (US); Rosa Crovetto, Wayne, PA (US); Wiley Lyle Parker, Conroe, TX (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/395,027

(22) Filed: Mar. 31, 2006

(65) Prior Publication Data

US 2007/0229095 A1 Oct. 4, 2007

(51) Int. Cl.
*G01R 27/08* (2006.01)
*G01N 17/04* (2006.01)

(52) U.S. Cl. .......................... 324/700; 422/53
(58) Field of Classification Search ............. 324/700
See application file for complete search history.

(56) References Cited

U.S. PATENT DOCUMENTS

| | | | |
|---|---|---|---|
| 3,731,297 A * | 5/1973 | Dunn et al. ............... 340/540 |
| 4,575,678 A * | 3/1986 | Hladky ...................... 205/776 |
| 4,780,664 A | 10/1988 | Ansuini et al. |
| 5,177,996 A * | 1/1993 | Sahakian ...................... 73/40 |
| 5,895,843 A * | 4/1999 | Taylor et al. .................. 73/86 |
| 5,896,034 A | 4/1999 | Marshall |
| 5,972,198 A * | 10/1999 | Takeuchi et al. ......... 205/776.5 |
| 6,054,038 A * | 4/2000 | Davis et al. ............. 205/776.5 |
| 6,131,443 A | 10/2000 | Duncan |
| 6,280,603 B1 | 8/2001 | Jovancicevic |
| 6,556,027 B2 * | 4/2003 | Banks ........................ 324/700 |
| 6,628,111 B2 * | 9/2003 | Shapiro et al. ............. 324/71.2 |
| 6,777,947 B2 * | 8/2004 | McCoy et al. .............. 324/449 |
| 6,946,855 B1 * | 9/2005 | Hemblade ................... 324/700 |

* cited by examiner

*Primary Examiner*—Andrew H. Hirshfeld
*Assistant Examiner*—John Zhu
(74) *Attorney, Agent, or Firm*—Wegman, Hessler & Vanderburg

(57) ABSTRACT

A corrosion monitoring device for monitoring corrosion in fluid containing systems and other equipment exposed to a corrosive environment comprising sensor elements having a composition substantially the same as the equipment being monitored, the sensor elements having a predetermined thickness for exposure to a corrosive solution of the fluid containing system. An electrical property of the monitoring device changes when corrosion penetrates through the thickness of the sensor element. A digital output device generates a first binary signal when corrosion has not penetrated through the thickness of the sensor elements, and a second binary signal when corrosion has penetrated through the thickness of the sensor elements. Multiple sensor elements may be used to provide multiple binary signals. Information from the digital outputs may be processed to provide a cumulative log of corrosion measurements.

11 Claims, 6 Drawing Sheets

METHOD AND APPARATUS FOR CORROSION DETECTION

BACKGROUND OF THE INVENTION

1. Field of the Invention

The present invention relates generally to a system and method for measuring corrosion, and more particularly relates to a system and method for detecting localized corrosion in vessels, piping, valves, pumps, and other equipment exposed to a corrosive environment based on the time required for corrosion to proceed through a predetermined thickness of corrosion sensor material.

2. Description of Related Art

Reliable corrosion monitoring of various process equipment is extremely important. For example, it is generally known that various industrial processes produce corrosive by-products. Such corrosive by-products frequently corrode industrial equipment, increase production costs, and create production delays. Thus, corrosion monitoring is a valuable tool which can alleviate such process upsets. Various attempts have been made using electrochemical (EC) and non-electrochemical techniques to identify corrosion processes. For example, linear polarization resistance (LPR) and electrochemical noise methods have been used to identify corrosion rates, types of corrosion, and parameters associated with localized corrosion. Other techniques include the application of electrical resistance (ER) measurements to determine loss of thickness and hence determine corrosion rates. Foil penetration methods have also been used to study the kinetics of pitting in aluminum and aluminum alloys. However, these methods have not been entirely satisfactory in providing an unambiguous method to determine the propagation of localized corrosion in a robust and cost effective manner.

One of the problems encountered with currently available corrosion monitoring methods and devices is that none of the methods provide reliable and unambiguous measures of the uniform corrosion rate or the rate of localized corrosion. The LPR technique typically only provides information on uniform corrosion conditions because it provides an average signal for the surface of the electrode being monitored. Depending upon the environment, metallic material, and corrosion type, the assumption that the corrosion rate is proportional to the measured charge transfer or polarization resistance is invalid when the corrosion is of a localized nature. It is known that localized corrosion (e.g. pitting) is a leading cause of system failure. With LPR, the instantaneous corrosion rate may vary by several orders of magnitude over a short time, and thus, the computed rate may or may not by itself produce much meaningful information. Moreover, due to the complex nature of the measurements and varying resistances involved, the rate at which the potential is scanned may have a significant effect on the amount of current produced at all values of potential sign. Such systems require precise measurements of small incremental changes in the electrical properties of the sensor device, thus making them quite susceptible to noise. Accordingly, such devices typically require relatively complex and expensive components, substantially increasing the cost of making and using such devices. A drawback of ER-type sensors is their considerable bulk due to the long length of the exposed strip necessary to make changes in resistance easily measurable. Although it may be possible to reduce the thickness of the strip, this will adversely impact sensor life because a reduced sensor thickness will corrode entirely through in a shorter period of time.

In view of these limitations, it would be desirable to provide a sensor system and method which is relatively simple and cost effective to manufacture and use, which is substantially robust to noise, and which is capable of measuring localized corrosion (i.e., pitting) with cumulative corrosion measurements.

SUMMARY OF THE INVENTION

The present invention provides a corrosion monitoring device adapted for monitoring corrosion in fluid containing systems and equipment. Although the present invention is described herein in terms of a corrosion monitoring device for use in fluid containing vessels and systems, the invention is also applicable for monitoring corrosion that occurs in valves, pumps, piping and any other equipment or material exposed to a corrosive environment. The present invention comprises at least one conductive sensor element fabricated from a conductive material having a composition substantially the same as the container or equipment being monitored. In one exemplary embodiment, a separator (i.e. insulator) element is located between a sensor element and a conductive backing element to form a layered sensor assembly. The sensor assembly is then installed in the fluid containing environment so as to expose the sensor element(s) to the processing fluid. An electric potential or current is applied between the sensor element and backing element. When the separator element remains dry, a virtual open circuit (high impedance) is provided between the sensor and backing elements, thereby inhibiting the flow of current through the device. Over time, a gradual loss of material occurs across the thickness of the sensor element due to the corrosive action of the processing fluid. Once the corrosion has penetrated through the predetermined thickness of the sensor element, the impedance between the sensor and backing elements is reduced, and the separator element becomes conductive due to wetting from exposure to the processing fluid, thus providing a virtual closed circuit and allowing current to flow through the device. The monitoring device communicates with a digital output device configured to output a first binary signal (e.g. ON, GO) indicating that corrosion has not penetrated through the thickness of the sensor element, and a second binary signal (e.g. OFF, NO-GO) indicating that corrosion has penetrated through the thickness of the sensor element. It is also understood that multiple sensor elements of various thicknesses may be used to extend the sensor life and/or provide a cumulative log of corrosion measurements over time. In this way, the present invention provides a substantially noise resistant and relatively simple digital signal approach to corrosion monitoring.

In another exemplary embodiment, the invention is carried out by mounting one or more conductive sensor elements on a substrate. In this embodiment, an electric potential or current is applied across the length of the sensor element(s). When the sensor element is first installed, the impedance of the sensor element is relatively low because the thickness of the sensor element is continuous, with results being that electrical current is free to flow through the length of the sensor element. Accordingly, the digital output device generates a first binary signal indicating that corrosion has not yet penetrated through the predetermined thickness of the sensor element. Over time, however, a gradual loss of material occurs across the thickness of the sensor element due to the corrosive action of the processing fluid. Once this corrosion has penetrated through a predetermined thickness of the sensor element, the impedance of the sensor element increases as the sensor element becomes discontinuous, thereby inhibiting the flow of current through the device. In this case, the digital output device outputs a second binary signal indicating that the impedance of the sensor element has increased beyond a predetermined threshold limit due to the corrosive action of the processing fluid over time. It is also understood that multiple sensor elements of different thicknesses may be used to provide multiple binary signals for each sensor element. In this way, multiple sensor elements function to extend the consumable life of the device and/or provide a cumulative log of corrosion measurements over time.

DETAILED DESCRIPTION OF THE INVENTION

The present invention relates to a system and method for detecting corrosion rates in fluid containing systems or other equipment exposed to a corrosive environment based on an indication of corrosion penetrating through a given thickness of an electrically conductive sensor element. Although the present invention is described herein in terms of a corrosion monitoring device for use in fluid containing vessels and systems, the invention is also applicable for monitoring corrosion that occurs in valves, pumps, piping and any other equipment or material exposed to a corrosive environment.

Figure 1A:
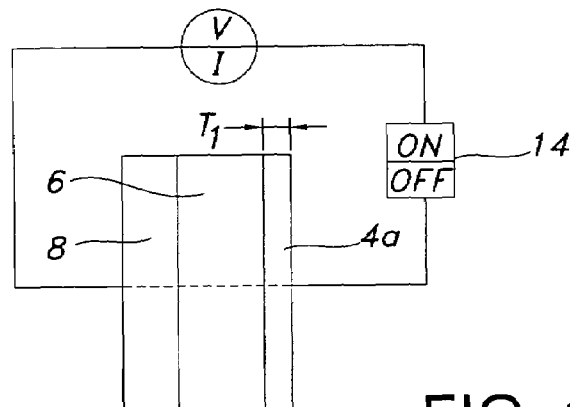
FIGS. 1A, 1B illustrate exemplary embodiments of a corrosion monitoring system in accordance with the present invention.
Figure 1B:
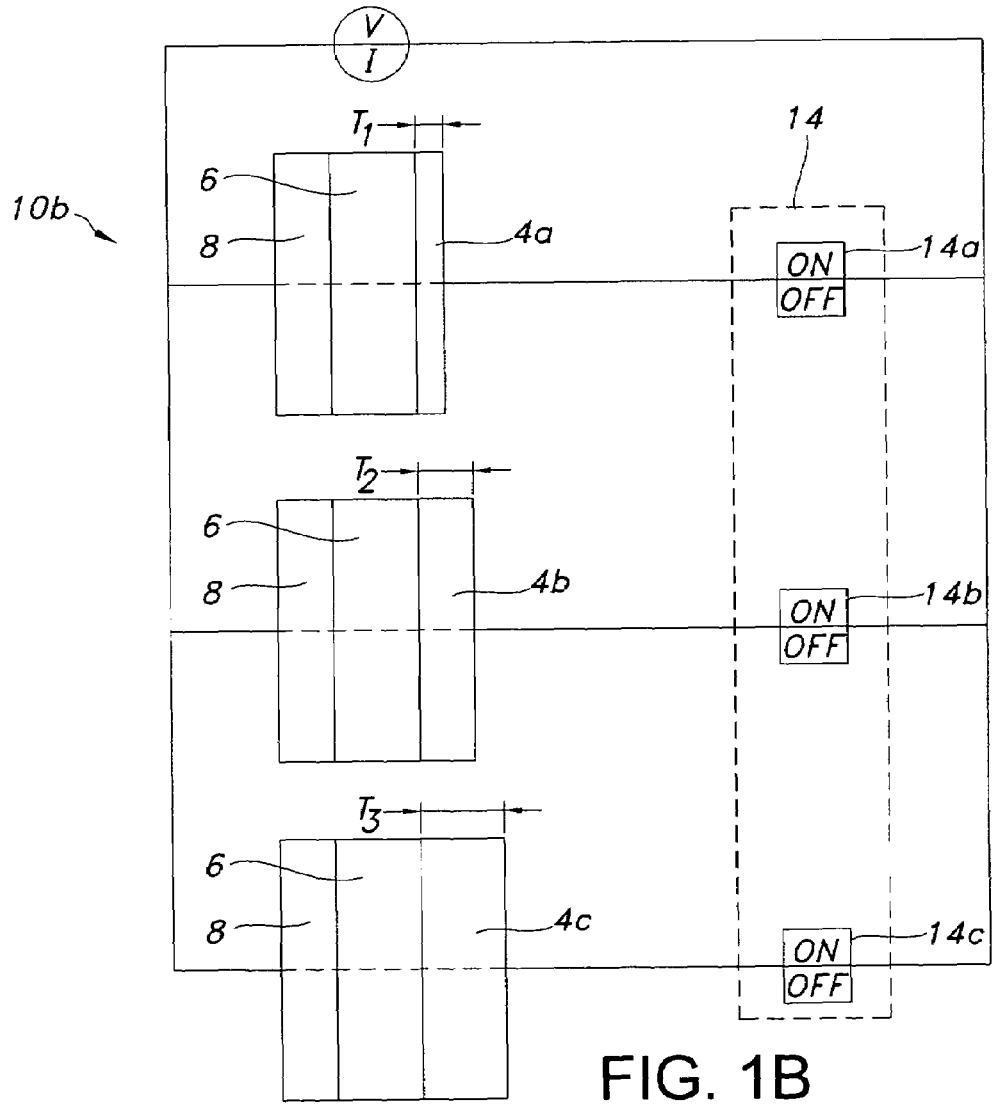

With reference to the exemplary embodiments of FIGS. 1A, 1B, a sandwich configuration of a sensor element 4a-c and a backing element 8 separated by an insulator 6 is employed to form a single integrated sensor assembly 10a as shown in FIG. 1A. By comparison, FIG. 1B illustrates an integrated sensor assembly 10b having multiple sensor elements 4a, 4b and 4c with different thicknesses $T_1$, $T_2$ and $T_3$ which may be incorporated into a single corrosion monitoring assembly 10b. One or more of the composite sensor assemblies 10a, 10b are installable into equipment which is susceptible to corrosion, such as fluid containing systems, valves, pumps, pipes and the like. The sensor elements 4a-c are then exposed to corrosion causing elements of the corrosive environment. The sensor elements 4a-c are preferably formed from a conductive metallurgical material having a composition substantially the same as the container or equipment being monitored. An electric potential or current is applied between the sensor elements and backing element 8. Initially, the impedance between the sensor elements 4a-c and backing element 8 is relatively high when corrosion has not penetrated through the thickness $T_{1-3}$ of the exposed sensor elements 4a-c due to the insulating properties of the separator element 6. That is, the separator element 6 keeps the sensor elements 4a-c and backing elements 8 isolated so long as the separator element 6 remains dry. As a result, the digital output device 14 is adapted to output a first binary signal (e.g. ON, GO) indicating that corrosion has not penetrated through the predetermined thickness of the sensor element. Over time, however, a gradual loss of material occurs across the thickness $T_{1-3}$ of the sensor elements 4a-c due to the corrosive action of corrosion causing elements and/or processing fluid. Once the corrosion has penetrated through the predetermined thickness of a particular sensor element 4a-c, the impedance of the separator element 6 decreases as it becomes conductive due to wetting from exposure to the processing fluid. In this case, the digital output device 14 outputs a second binary signal (e.g. OFF, NO-GO) indicating that corrosion has penetrated through the respective thickness $T_{1-3}$ of a particular sensor element 4a-c. When corrosion proceeds through the thickness of an exposed sensor element, the separator element 6 comes in contact with the processing fluid electrolyte, with results being that an electrical property (e.g. impedance, resistance, capacitance, voltage, current) between the sensor and backing elements 4a-c, 8 changes sharply. Although the present invention contemplates monitoring impedance across the sensor device, it is also understood that virtually any electrical property could be monitored to obtain the same or similar results.

In the exemplary embodiments described herein, when corrosion proceeds through the exposed sensor elements 4a-c and brings the separator element 6 in contact with the electrolyte of the processing fluid, the separator element 6 becomes conductive and the impedance between the sensor elements 4a-c and backing element 8 decreases sharply. A digital output device 14 is employed to provide a binary ON/OFF signal associated with this sharp change to indicate whether corrosion has penetrated through the predetermined thickness of a particular sensor element 4a-c. It is understood that a visual indicator in the form of an LED (not shown) or other display means may be used in a manner known in the art to provide an indication of corrosion penetration events. It is also understood that the binary signals can be output to a computer (not shown) for data processing to provide additional control information, such as a cumulative log of corrosion measurements over time. In this way, the predetermined thickness of the respective sensor elements 4a-c may be used to predict the time required for corrosion to penetrate a given thickness of the container being monitored. The relatively simple digital signal approach of the present invention is advantageous in that it allows the monitoring device to be substantially robust to noise, and it is possible to obtain useful information regarding the time for corrosion to propagate through a given thickness of the equipment under test without having to precisely measure small incremental changes in electrical properties as presently known in the art. Instead, the present invention is only concerned with measuring sharp step changes in the electrical properties of the sensor device 10a, 10b, thereby allowing the corrosion monitoring devices of the present invention to be economically manufactured with relatively simple components which are not concerned with precise measurements of small incremental changes over time and are not concerned with calibrating small fluctuations due to noise.

Referring now to FIG. 1B, it is shown that multiple sensor elements 4a, 4b and 4c having different thicknesses $T_1$, $T_2$ and $T_3$ may be integrated into a single corrosion monitoring device 10b. Each sensor element 4a-c communicates with the digital output device 14, thus providing multiple digital output signals 14a-c indicative of whether corrosion has penetrated through the thickness of the respective sensor element 40a, 40b and 40c. One advantage of the configuration of FIG. 1B is that multiple sensor elements may be used to extend the consumable life of the monitoring device 10b and will provide a cumulative log of corrosion measurements over time since each sensor element will become consumed at a different point in time.

To facilitate installation of the monitoring device in the fluid containing system, the exemplary sensor assemblies of the present invention may be integrated into a pipe screw arrangement in a manner known in the art to enable threading the sensor assembly into the fluid container for monitoring purposes. It is also understood the sensor assemblies could be integrated into a dip-stick type probe apparatus for insertion into the processing fluid. It is also contemplated that the sensor assemblies could be incorporated into a bypass structure which temporarily directs processing fluid to an off-line environment for testing. Those skilled in the art will also appreciate that other known or later developed methods for installing the sensor assemblies into the fluid containing system could be used to achieve the same or similar results.

The following examples are included to demonstrate the broad applicability of the present invention. It should be appreciated by those of skill in the art that the techniques disclosed in the examples which follow represent techniques discovered by the inventors, and thus can be considered to constitute exemplary modes for its practice. However, those of skill in the art should, in light of the present disclosure, appreciate that many changes can be made in the specific embodiments which are disclosed and still obtain a like or similar result without departing from the scope of the invention.

EXAMPLE 1

Figure 2:
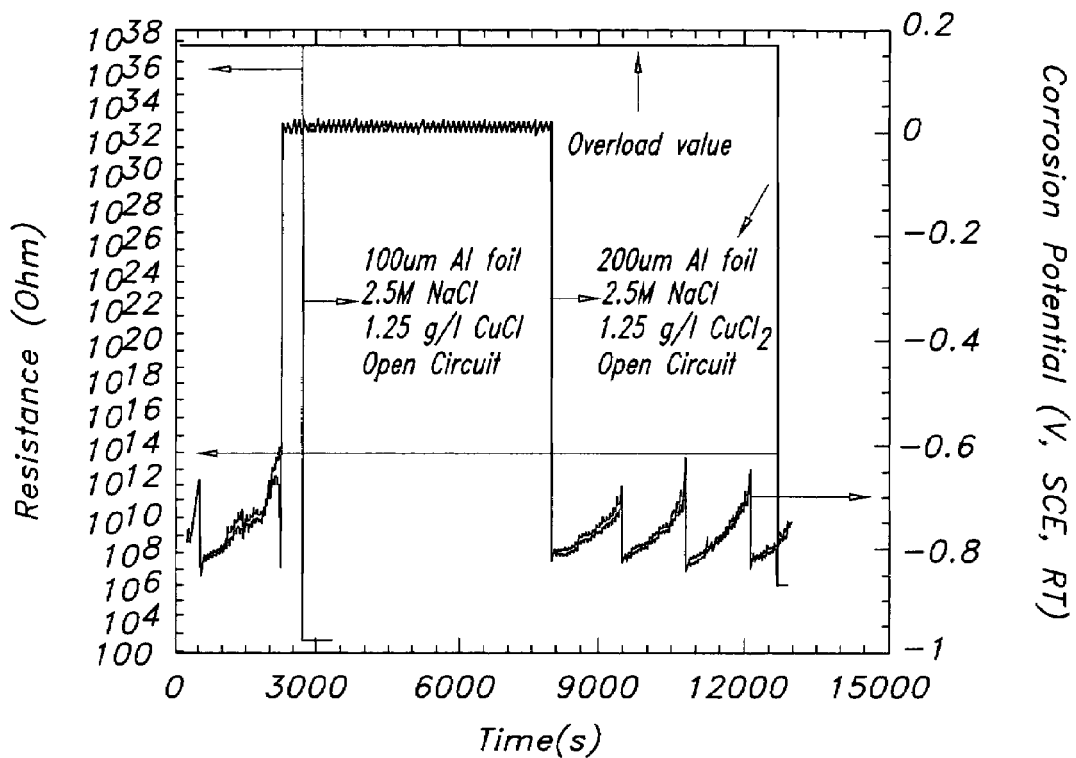
FIG. 2 is a graphical representation of resistance/potential versus time raw data plot illustrating change in resistance of aluminum foils of two different thicknesses when corrosion penetrates through the thickness of each aluminum foil, respectively.

An aluminum foil of thickness 0.2 mm was exposed to 2.5M NaCl containing 1.25 g/l $CuCl_2$. The resistance between the Al foil exposed to solution and another Al foil not exposed to solution are measured as a function of time. Initially the resistance is very high (in fact it is higher than the maximum value that the instrument can measure 110 MΩ). When corrosion has penetrated through the thickness of the exposed foil, there is a sharp change in resistance as seen in FIG. 2. Thus the time for corrosion to proceed through a given thickness can be determined. The time for corrosion to proceed through various thickness can also be measured to determine the kinetics of corrosion propagation as shown in FIG. 2 where foils of two different thickness were tested 0.1 mm and 0.2 mm.

EXAMPLE 2

Figure 3:
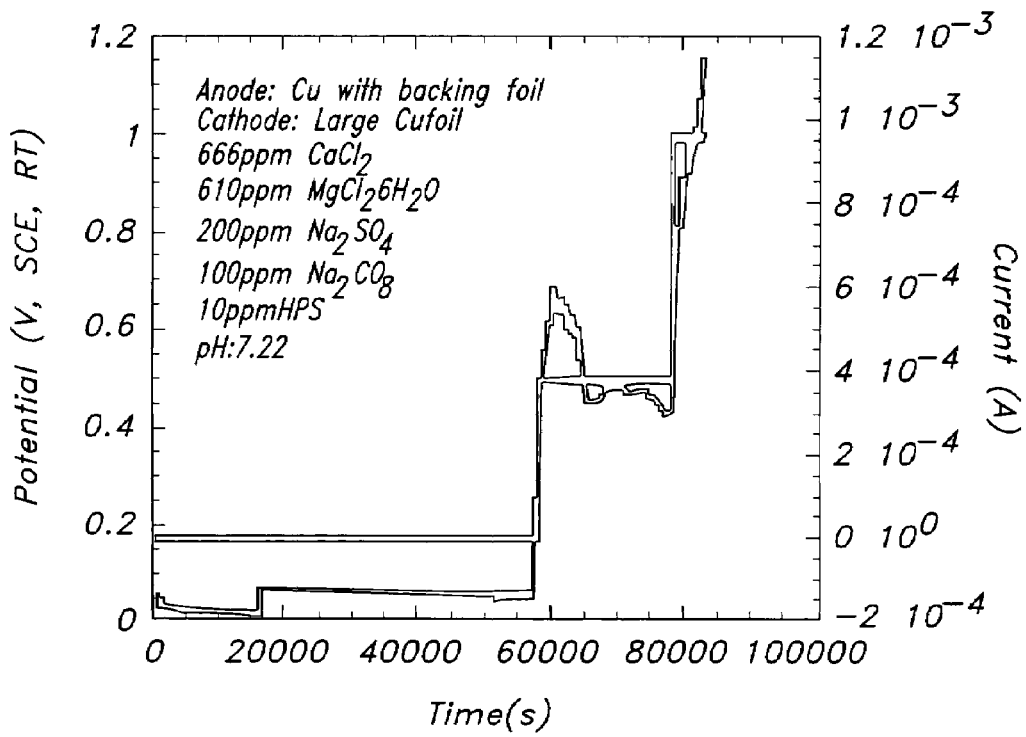
FIG. 3 is a graphical representation of potential/current versus time raw data plot illustrating potential steps applied to a copper sample.
Figure 4:
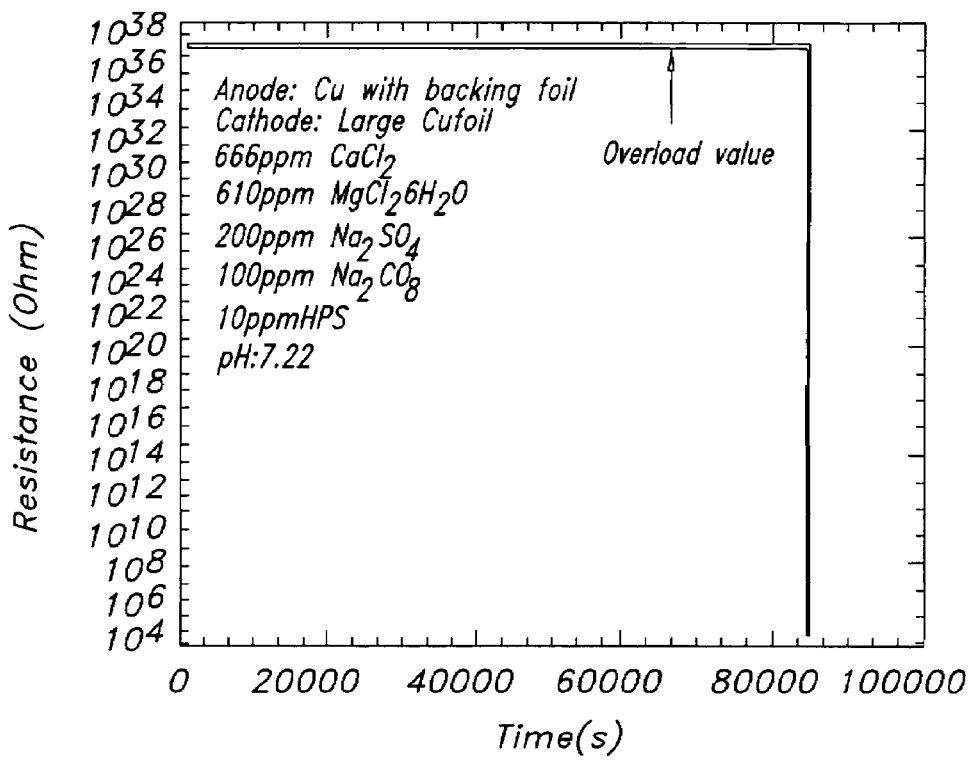
FIG. 4 is a graphical representation of resistance versus time raw data plot illustrating change in resistance of copper foil assembly indicating corrosion propagation through the thickness of the foil.
Figure 5:
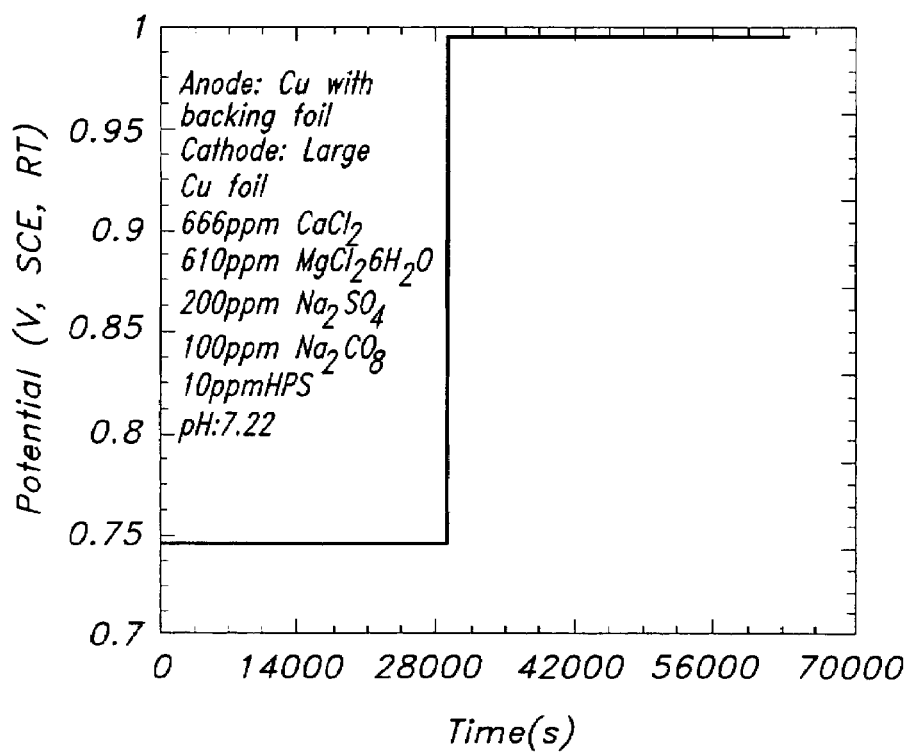
FIG. 5 is a graphical representation of potential versus time raw data plot illustrating potential steps applied as a function of time on copper samples.
Figure 6:
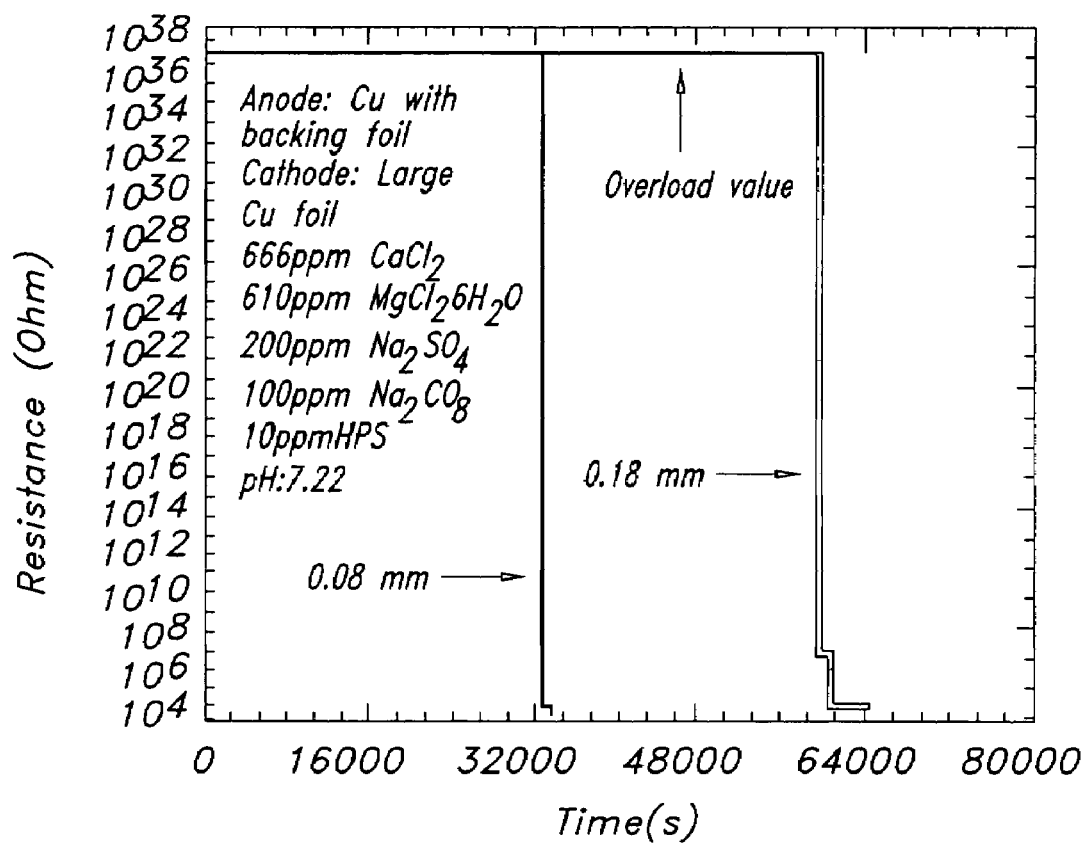
FIG. 6 is a graphical representation of resistance versus time raw data plot illustrating change in resistance of copper foils of two different thicknesses when corrosion penetrates through the thickness of each copper foil, respectively.

Copper foils of two different thickness were tested in the solution chemistry shown in Table 1 below. An anodic potential of 0.5 V SCE and 1V SCE was applied using a three electrode setup. FIG. 3 is a graphical representation of potential and current versus time raw data plot illustrating the potential steps applied to the copper sample over the course of the experiment. The resistance is also measured and a change in resistance is indicative of corrosion penetrating through the thickness of the foil as shown in FIG. 4. In another set of experiments on copper foils of two different thickness (0.08 mm and 0.18 mm), potential steps were applied shown in FIG. 5. FIG. 6 demonstrates that resistance changes sharply when corrosion penetrates through the thickness of the foil.

TABLE 1

| Solution chemistry used in copper foil experiment. | |
|---|---|
| $CaCl_2$ | 666 ppm |
| $MgCl_2 \cdot 6H_2O$ | 610 ppm |
| $Na_2CO_3$ | 100 ppm |
| $Na_2SO_4$ | 200 ppm |
| $PO_4^{2-}$ (as $Na_4P_2O_7$) | 2.5 ppm |
| $PO_4^{2-}$ (as $NaHPO_4$) | 15 ppm |
| HPS | 10 ppm |

Figure 7:
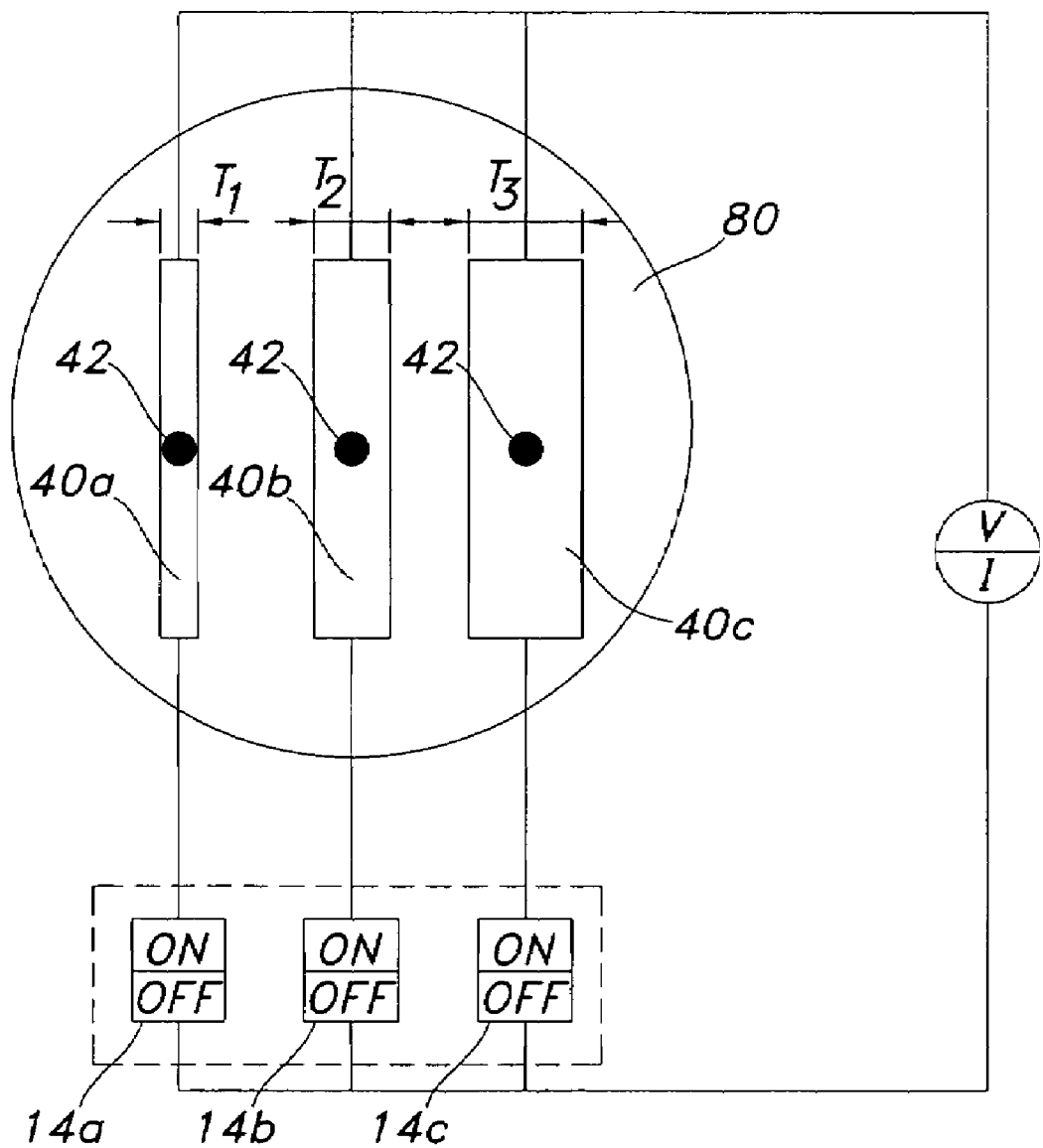
FIG. 7 illustrates another exemplary embodiment of a corrosion monitoring system in accordance with the present invention, showing corrosion penetrating through the thickness of the sensor elements.
Figure 8:
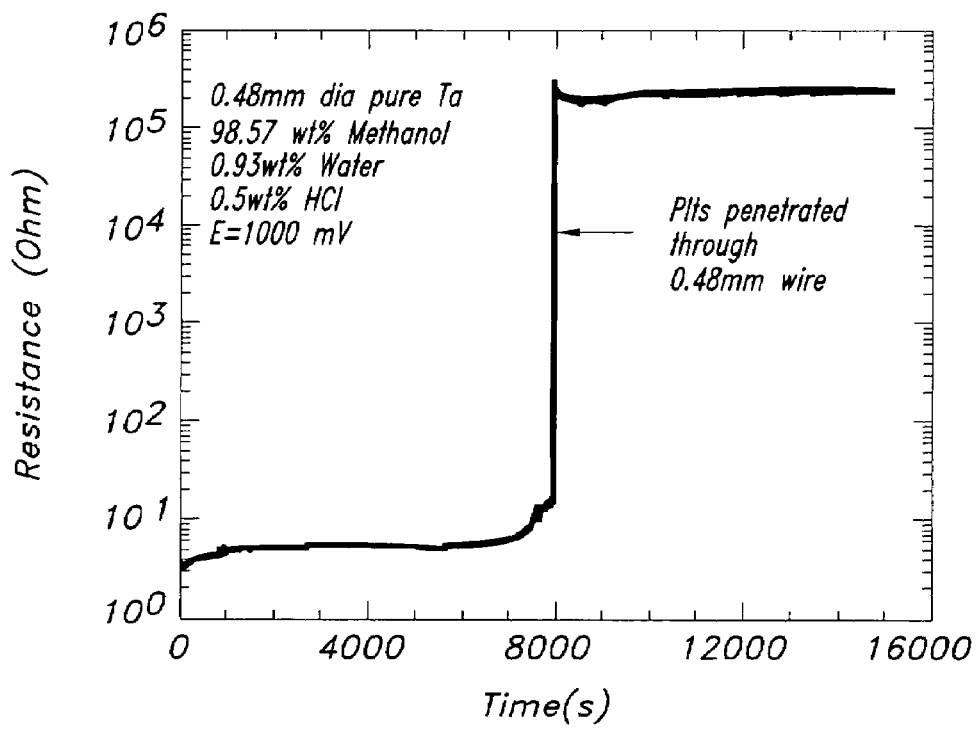
FIG. 8 is a graphical representation of resistance versus time raw data plot of tantalum wire configured in accordance with FIG. 7 upon exposure in methanol environment containing HCI and water.

Turning now to FIG. 7, which illustrates another exemplary embodiment of the present invention, there is shown multiple sensor elements 40a, 40b and 40c disposed in spaced apart relation on a backing member or substrate 80. Each sensor element has a different thickness $T_1$, $T_2$, $T_3$ corresponding to a predetermined amount of loss due to corrosive action when the sensor elements are exposed to the processing fluid. The sensor elements are formed of conductive material having a composition substantially the same as the container being monitored. At least one sensor element is then mounted on a substrate 80, an electric potential is applied across the lengths of the sensor elements 40a-c, and the resistance of the sensor elements is measured continuously. As best shown in FIG. 8, the resistance of the sensor elements 40a-c is relatively low when the elements are continuous. However, once corrosion penetrates through the metal, there is a sharp change in resistance. Samples of several different thicknesses $T_1$, $T_2$, $T_3$ of sensor material can be exposed to provide a cumulative log for processing control and to determine the rate of corrosion propagation. It is understood that various types of electrochemical measurements can be performed on the samples to accelerate corrosion and evaluate the effect of the various process parameters in situ.

Referring again to FIG. 7, sensor element 40c is substantially continuous because corrosion 42 has not penetrated through the entire thickness $T_3$ of the sensor element, thus allowing electrical current to flow through the sensor element 40c. In turn, the digital output device 14 generates a visual indicator 14c in the form of a binary ON or OFF signal indicating that corrosion has not completely penetrated the predetermined thickness $T_3$ of the sensor element 40c. The visual indicator may be in the form of an LED or other go, no-go type signal indicator. By comparison, sensor elements 40a and 40b are substantially discontinuous because corrosion 42 has substantially penetrated through the entire thicknesses $T_1$, $T_2$ of sensor elements 40a and 40b. As a result, an open circuit preventing the flow of current through elements 40a, 40b is provided. In turn, the digital output device 14 generates visual indicators 14a, 14b indicating that current is no longer flowing through sensor elements 40a, 40b due to corrosion having penetrated through the predetermined thickness of the sensor elements 40a, 40b. In this way, the digital output device 14 outputs first binary signals 14a, 14b indicating that corrosion has penetrated through the thicknesses $T_1$ and T$_2$ of the sensor elements 40a and 40b, and a second binary signal 14c indicating that corrosion has not penetrated through the thickness T$_3$ of sensor element 40c, thus providing a progressive series of GO/NO-GO digital signals as corrosion progresses through the various thicknesses of the sensor elements. It is noted that although three sensor elements 40a, 40b and 40c are shown in FIG. 7, those skilled in the art will appreciate that more or less than three sensor elements with different thicknesses could also be used without departing from the broader spirit of the present invention.

The embodiment of FIG. 7 comprises measuring the electrical resistance of a thin metal wire/strip/sheet sensor element 40a-c. The resistance of the sensor elements 40a-c is relatively low when it is substantially continuous as exemplified by sensor element 40c. However, when corrosion proceeds substantially through the thickness of the sensor elements, the resistance being measured increases sharply since the continuity of the conductive sensor elements 40a, 40b is broken. This step change in resistance can be used to determine the time for corrosion to penetrate through a given thickness as shown by the following Example 3.

EXAMPLE 3

A tantalum wire of 0.48 mm thickness was exposed to a methanol solution containing 0.93 wt % water and 0.5 wt % HCl. A potential of 1000 mV Ag/AgCl/0.1M KCl was applied to accelerate corrosion. The resistance of the wire was measured continuously. Initially when the wire was continuous, the resistance was low as shown in FIG. 8. However, when pits or corrosion propagate through the diameter of the wire there is a sharp change in the resistance of the wire from about 10Ω to about 10MΩ.

Figure 9:
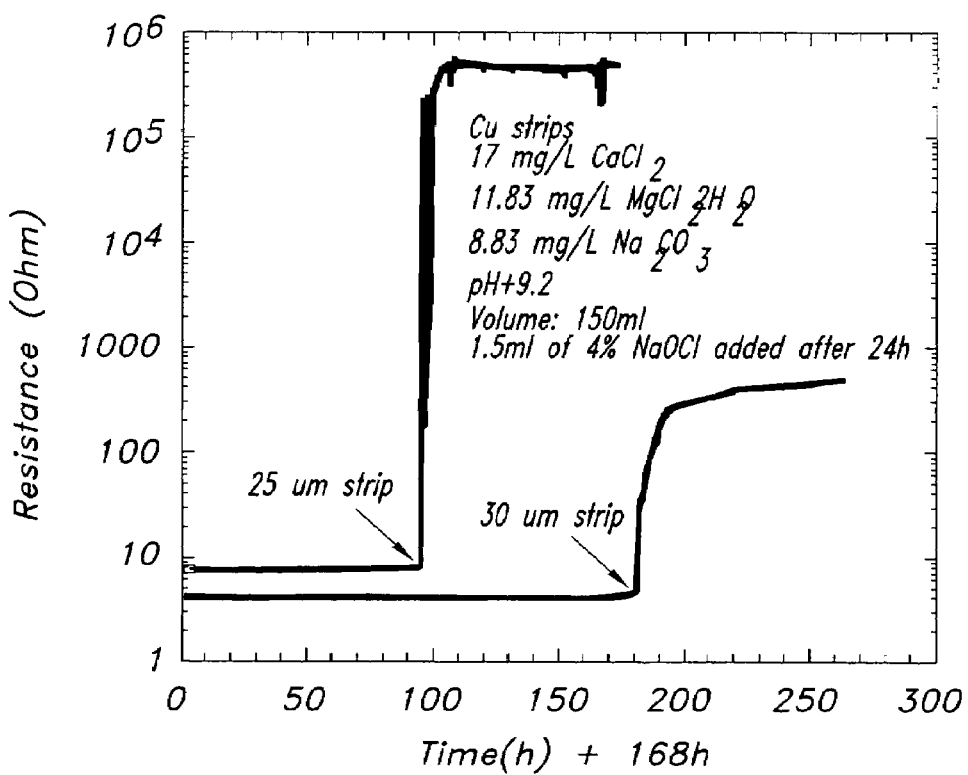
FIG. 9 is a graphical representation of the resistance versus time raw data plot of copper strips configured in accordance with FIG. 7 upon exposure in chloride containing environment.

It is noted that the embodiment of FIG. 7 differs from the embodiments of FIGS. 1A, 1B and 9 in that electrical current initially flows through the sensor elements 40a, 40b, and 40c from the time the device is first installed in the fluid containing system, and current will continue to flow through the sensor elements 40a, 40b and 40c until the loss of thickness in the respective sensor elements due to corrosive activity. As shown in FIG. 9, the 25 and 30 micron strips have failed, while corrosion in the 40 micron strip is still in progress. This shows we are able to pick up step changes in resistance due to discontinuity created by pitting.

One consequence of this exemplary design is that electrical power is being continuously dissipated in the sensor device prior to the time that corrosion has penetrated through the entire thickness of the sensor elements. In contrast, electrical power is not being dissipated in the embodiments of FIGS. 1A, 1B prior to the time that corrosion penetrates through the entire thickness of the sensor elements, thus advantageously reducing the overall power being consumed by the monitoring device during the time it takes for corrosion to penetrate through the predetermined thicknesses of the sensor elements 4a-c.

As described herein, the exemplary embodiments of the present invention provide a simple binary ON/OFF signal indicative of whether corrosion has penetrated through the entire thickness of a conductive sensor element. By monitoring only sharp changes in the electrical properties of the monitoring device which occur when corrosion penetrates through a given thickness of the sensor elements, the sensor system of the present invention is substantially more robust to noise than prior art corrosion monitoring systems, thereby allowing the device to be relatively simple and inexpensive to manufacture, while also being capable of measuring localized corrosion (i.e., pitting) and providing cumulative corrosion measurements. Measuring step changes in an electrical property of the device can be used to determine the time for corrosion to penetrate through a given thickness. The systems and methods described in this invention will be able to determine the rate of propagation of corrosion unambiguously, independent of the form of corrosion and type of environment in which measurements need to be made, and is substantially robust to noise, making the device relatively inexpensive to manufacture and easy to use.

The advantages of the present corrosion monitor as described herein are numerous. The monitor of the present invention provides a method of detecting the time required for corrosion to propagate through a given thickness independent of the nature of the electrolyte causing corrosion. The time to propagate through various thickness can then be processed to give the kinetics of corrosion propagation. The application of various electrochemical techniques to the samples can accelerate corrosion and determine the role of various factors, and the effectiveness of inhibitors on the rate of corrosion propagation can be studied and predicted.

While the disclosure has been illustrated and described in typical exemplary embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the scope of the disclosure as defined by the following claims.

What is claimed is:

1. A corrosion monitoring device for monitoring corrosion in equipment, comprising:
   a sensor element having a composition substantially the same as the equipment being monitored, said sensor element having a predetermined thickness;
   a backing element;
   a separator element disposed between said sensor element and said backing element, thereby forming a sensor assembly;
   a means for exposing said sensor element to a corrosion causing solution, wherein said sensor element undergoes a gradual loss of said predetermined thickness due to corrosive action of said solution;
   a means for applying an electric potential or current across said sensor assembly, wherein said separator element is configured to have a first impedance when corrosion has not penetrated through the thickness of said sensor element, and wherein said first impedance is reduced when said corrosion has penetrated through the thickness of said sensor element; and
   a digital output means for generating a binary signal having a first state when corrosion has not penetrated through the thickness of said sensor element and a second state when corrosion has penetrated through the thickness of said sensor element.

2. The device as recited in claim 1, further comprising multiple sensor assemblies disposed in spaced apart relation, each said sensor element comprising a different predetermined thickness, said digital output means being configured to generate a binary signal associated with each said sensor assembly.

3. The device as recited in claim 2, further comprising a display unit for indicating a status of said binary signal.

4. The device as recited in claim 3, further comprising a processing means for processing said binary signals to reveal information about the time required for corrosion to penetrate through said equipment.

5. A method for monitoring corrosion in equipment, comprising the steps of:
  providing a sensor element having a composition substantially the same as the equipment being monitored, said sensor element having a predetermined thickness;
  providing a backing element;
  providing a separator element disposed between said sensor element and said backing element, thereby forming a sensor assembly;
  exposing said sensor element to a corrosion causing solution, wherein said sensor element undergoes a gradual loss of said predetermined thickness due to corrosive action of said solution;
  applying an electric potential or current across said sensor assembly, wherein said separator element is configured to have a first impedance when corrosion has not penetrated through the thickness of said sensor element, and wherein said first impedance is reduced when said corrosion has penetrated through the thickness of said sensor element; and
  generating a binary signal having a first state when corrosion has not penetrated through the thickness of said sensor element and a second state when corrosion has penetrated through the thickness of said sensor element.

6. The method as recited in claim 5, further comprising the steps of:
  applying electrochemical signals to said sensor element so as to measure electrochemical parameters including linear polarization, resistance and electrochemical noise; and
  applying electrochemical potentials to activate or inhibit the corrosion process.

7. The method as recited in claim 5, comprising the step of providing multiple sensor assemblies disposed in spaced apart relation, each said sensor element comprising a different predetermined thickness, said digital output means being configured to generate a binary signal associated with each said sensor assembly.

8. A corrosion monitoring device for monitoring corrosion in equipment, comprising:
  a sensor element having a composition substantially the same as the equipment being monitored; said sensor element having a predetermined thickness and a longitudinal length;
  a substrate coupled to said sensor element;
  a means for exposing said sensor element to a corrosion causing solution, wherein said sensor element undergoes a gradual loss of said predetermined thickness due to corrosive action of said solution;
  a means for applying an electric potential or current across said length, said sensor element having a first impedance when corrosion has not penetrated through the thickness of said sensor element, said sensor element having a second impedance when said corrosion has penetrated through the thickness of said sensor element, wherein said second impedance is greater than said first impedance; and
  a digital output means for generating a binary signal having a first state when corrosion has not penetrated through the thickness of said sensor element and a second state when corrosion has penetrated through the thickness of said sensor element;
  said device further comprising multiple sensor elements coupled to said substrate, each said sensor element comprising a different predetermined thickness, said digital output means being configured to generate a binary signal associated with each said sensor assembly.

9. The device as recited in claim 8, further comprising a display unit for indicating a status of said binary signal.

10. The device as recited in claim 9, further comprising a processing means for processing said binary signals to reveal information about the time required for corrosion to penetrate through said equipment.

11. A method for monitoring corrosion in equipment, comprising the steps of:
  providing a sensor element having a composition substantially the same as the equipment being monitored, said sensor element having a predetermined thickness;
  providing a substrate for mounting said sensor element;
  exposing said sensor element to a corrosion causing solution, wherein said sensor element undergoes a gradual loss of said predetermined thickness due to corrosive action of said solution;
  applying an electric potential or current across said length, said sensor element having a first impedance when corrosion has not penetrated through the thickness of said sensor element, said sensor element having a second impedance when said corrosion has penetrated through the thickness of said sensor element, wherein said second impedance is greater than said first impedance; and
  generating a binary signal having a first state when corrosion has not penetrated through the thickness of said sensor element and a second state when corrosion has penetrated through the thickness of said sensor element; and
  providing multiple sensor elements coupled to said substrate, each said sensor element comprising a different predetermined thickness, said digital output means being configured to generate a binary signal associated with each said sensor assembly.

* * * * *